United States Patent
Wagner et al.

(10) Patent No.: US 10,201,271 B2
(45) Date of Patent: Feb. 12, 2019

(54) EYE MEASUREMENT

(71) Applicant: Haag-Streit AG, Koeniz (CH)

(72) Inventors: Jörg Wagner, Oberdorf (CH); Lucio Robledo, Bern (CH); Philippe Cattin, Windisch (CH)

(73) Assignee: HAAG-STREIT AG, Koeniz (CH)

( * ) Notice: Subject to any disclaimer, the term of this patent is extended or adjusted under 35 U.S.C. 154(b) by 0 days.

(21) Appl. No.: 15/456,332

(22) Filed: Mar. 10, 2017

(65) Prior Publication Data
US 2017/0258318 A1 Sep. 14, 2017

(30) Foreign Application Priority Data
Mar. 11, 2016 (EP) .................................... 16159900

(51) Int. Cl.
*A61B 3/00* (2006.01)
*A61B 3/10* (2006.01)
*A61B 3/113* (2006.01)
*G01B 9/02* (2006.01)

(52) U.S. Cl.
CPC ............ *A61B 3/0025* (2013.01); *A61B 3/102* (2013.01); *A61B 3/1025* (2013.01); *A61B 3/113* (2013.01); *G01B 9/02077* (2013.01); *G01B 9/02091* (2013.01); *G01B 2290/65* (2013.01)

(58) Field of Classification Search
CPC ....... A61B 3/113; A61B 3/0025; A61B 3/112; G06K 9/00604; G06K 9/00597
USPC .................................................. 351/200–246
See application file for complete search history.

(56) References Cited

U.S. PATENT DOCUMENTS

| 8,403,481 | B2 | 3/2013 | Izatt et al. | |
|---|---|---|---|---|
| 9,101,294 | B2 | 8/2015 | Bagherinia et al. | |
| 2013/0335706 | A1* | 12/2013 | Schmitt-Manderbach | A61B 3/1005 351/221 |
| 2016/0106588 | A1* | 4/2016 | Srinivasan | A61F 9/00825 606/5 |
| 2016/0128565 | A1* | 5/2016 | Meznaric | A61B 3/107 351/212 |

FOREIGN PATENT DOCUMENTS

EP 3 021 071 A1 5/2016

OTHER PUBLICATIONS

Hong et al., "Eye motion corrected OCT imaging with Lissajous scan pattern", Proc. of SPIE vol. 9693 96930P-1.
Martinez-Graullera et al., "2D array design based on Fermat spiral for ultrasound imaging", Ultrasonics 50 (2010), pp. 280-289.

* cited by examiner

*Primary Examiner* — Mohammed Hasan
(74) *Attorney, Agent, or Firm* — Birch, Stewart, Kolasch & Birch, LLP

(57) ABSTRACT

In a method for interferometrically capturing measurement points of a region of an eye, a plurality of measurement points are captured by a measurement beam along a trajectory, wherein the same trajectory is passed over by the measurement beam in the region during at least a first iteration and a second iteration. The trajectory of the first iteration is rotated through an angle and/or displaced by a distance in relation to the trajectory of the second iteration in order to obtain a more homogeneous measurement point distribution.

21 Claims, 2 Drawing Sheets

EYE MEASUREMENT

TECHNICAL FIELD

The invention relates to a method for interferometrically capturing measurement points of a region of an eye, wherein a plurality of measurement points are captured by a measurement beam along a trajectory, wherein the same trajectory is passed over by the measurement beam in the region during at least a first iteration and a second iteration. Further, the invention relates to an apparatus for carrying out the method.

BACKGROUND OF THE INVENTION

Prior Art

The present invention relates to the interferometric capture of measurement points on a region of an eye.

Corresponding methods and apparatuses are known in ophthalmology. Typically, an interferometer is used to carry out such examinations of the eye. By way of example, OCT (optical coherence tomography) scanners are used as interferometers; these scan the eye at discrete positions in the lateral direction and, in the process, capture stray-light profiles (axial profiles) of the eye along the optical beam. On account of the axial profiles, it is possible to define three-dimensional measurement points in the eye, which preferably represent one or more optical surfaces.

By way of example, Zeiss (U.S. Pat. No. 9,101,294 B2) discloses a method for processing data from an OCT device, wherein an increase in the precision of the calculation of ocular measurements is intended to be achieved by different approaches. The methods comprise novel scanning patterns, the use of techniques for determining the transversal eye movement and an improved algorithm for eye movement correction.

In particular, the method comprises capturing a first small set of data by means of OCT and using the data to model the cornea. The model is subsequently used to create a precise, movement-corrected model during a further measurement with a more dense number of measurement points.

Further, Duke (U.S. Pat. No. 8,403,481 B2) discloses a method for reducing movement artifacts in OCT measurements. In the method, data are ascertained using a scanning pattern, said data being distributed in such a way that at least certain spatially adjacent data points were not ascertained in sequence. To this end, use can be made of a scanning pattern in which spatially adjacent data points are ascertained in non-sequential fashion. By way of example, the sample may be scanned by a number of series of scanning lines, with some of the scanning lines lying between previously measured scanning lines.

Essential requirements of the measurement, particularly when measuring the eye, are, firstly, a short overall duration of the measurement and a high resolution, i.e. a large coverage of the area to be measured. The short overall duration is an essential criterion, in particular on account of the unavoidable movements of the eye during the measurement.

The known methods are disadvantageous in that the measurements take a relatively long time. On account of the relatively long measurement duration, there is an increased risk of the measurement results being influenced by eye movements of the patient, as a result of which only inaccurate measurement results are able to be obtained.

SUMMARY OF THE INVENTION

It is an object of the invention to develop a method for interferometrically capturing measurement points on a region of an eye, which facilitates a particularly precise measurement of the eye, said method belonging to the technical field set forth at the outset, wherein, in particular, eye movements may be corrected in a particularly ideal manner.

The solution to the object is defined by the features of claim 1. In accordance with the invention, the trajectory of the first iteration is rotated through an angle and/or displaced by a distance in relation to the trajectory of the second iteration in order to obtain a more homogeneous measurement point distribution.

The object according to the invention is likewise achieved by an apparatus for carrying out such a method.

In principle, a distance measurement, in particular an axial distance measurement in the Z-direction (see below), particularly preferably an axial scattering profile (a so-called A-scan) along the beam direction forms the basis of the measurement method. The measurement points are preferably captured by means of spectral domain OCT (SD-OCT) or swept source OCT (SS-OCT), preferably with a temporally constant frequency. Methods using OCT have become established in ophthalmology as these may be used in scattering objects such as an eye and, in particular, have a relatively high penetration depth with, at the same time, a high axial resolution.

Different optical frequencies are used in SD-OCT. The light is dispersed and analyzed by means of a CCD or CMOS sensor. Using this, the full measurement depth may be achieved by a single measurement. By contrast, the optical frequency is periodically tuned in SS-OCT and the interference signal is measured resolved in time. These techniques are sufficiently well known to a person skilled in the art.

Distances may be captured by peak detection in the A-scan, edge detection in the A-scan or by a segmentation of sequentially captured A-scans.

In variants, use may also be made of other techniques for the point distance measurement or for the axial profile measurement (capturing of A-scans) (see interferometer), for example a time-of-flight measurement by means of a laser or the like.

Below, X, Y and Z-coordinates are used as a three-dimensional orthogonal system. The trajectory is preferably considered along an XY-plane and the measurement beam has the Z-direction in at least one measurement direction, in particular in the direction of a midpoint of the region. From this position, the measurement beam may either be displaced in parallel, i.e. maintaining the Z-direction, or else be swiveled through an angle in the X-direction and a second angle in the Y-direction. Furthermore, the change in position may also be achieved by a combination of these variants. Provided nothing else is mentioned, the preferred first variant is assumed below, without there being a restriction to one of the variants. To this end, provision may be made of telecentric optical units, in which a beam offset may be in parallel. The distance measurement relates to the Z-axis or the direction of the measurement beam, wherein changes in the refractive index along the measurement axis may lead to refractive effects, which could lead to changes in the direction and scaling of the axial scattering profile. Methods for geometric correction and conversion of the measured lengths are known to a person skilled in the art.

The trajectory is respectively understood to be a plane projection in an XY-plane, which intersects the eye to be measured or which has a small distance from the eye to be measured. In practice, the trajectory may deviate from this description depending on the eye to be measured. By way of example, if points are captured along a trajectory at regular intervals by means of the measurement beam, these points are only at a constant distance from one another in the measurement region if the measurement region is a plane parallel to the plane projection. However, if this trajectory is projected onto an eye, temporally successive measurement points near the center lie closer to one another than temporally successive measurement points in the edge region of the eye.

An axial length profile or A-scan should be understood to mean a profile of the eye along the z-axis or the beam direction. A B-scan is understood to mean an axial profile along a straight section through the eye, which is composed of individual A-scans. The axial length profiles may be combined to form a three-dimensional model of the eye or a section through the eye. However, the data may also be used differently, for example for simulating a beam path, a correction lens or the like.

Below, the region of the eye need not necessarily be understood to mean the surface of the cornea but, in particular, may also be understood to be a three-dimensional region. Thus, depth profiles of the eye may be created with the aid of OCT methods, which equally fall under the term "region" below.

The degree of coverage is the proportion of the area to be measured in which the distance from any point to the closest measurement point does not exceed a critical value. For measurements of the topography of the eye, a degree of coverage of 100% is usually required, wherein the area to be measured should have at least a diameter of 7.5 mm and the critical distance should be 0.5 mm. However, depending on the requirements, it is also possible to use lower degrees of coverage or smaller measurement areas, for example when realizing shorter measurement times. The areas and distances relate to the XY-plane in which the trajectory is defined.

The more homogeneous measurement point distribution is understood to mean an increased degree of coverage when compared with a second iteration without rotation or displacement of the trajectory. Hence, the more homogeneous measurement point distribution is obtained, in particular, if at least one measurement point of the second iteration does not come to rest on a measurement point of the first iteration.

Below, the trajectory is defined in relation to the XY-plane as a two-dimensional curve should nothing else be specified. However, it is clear to a person skilled in the art that the trajectory typically represents a three-dimensional spatial curve which is distorted in relation to the trajectory when applied as a projection onto a body. However, since this spatial curve depends both on the trajectory form and on the body form and therefore is able to vary over a large range, this is not discussed in any more detail. Moreover, the trajectory need not necessarily follow a function or definition in a mathematically exact manner. Preferably, the trajectory has a form which lies on the above-described trajectory, or on one of the above-described trajectories, for at least the individual measurement points. In this case, the functions or the forms are ultimately only defined by an interpolation of the measurement points. In practice, the measurement points may, however, also deviate slightly from the trajectory. Depending on the number of measurement points and size of the object, the mean deviation from the trajectory may e.g. be less than 5%, preferably less than 1%, of the diameter of the circumference of the area to be measured.

Below, an iteration is understood to mean the capture of measurement points on the trajectory, with the trajectory being passed over exactly once in the entirety thereof. Instead of the term "iteration", use is also made of the equivalent term "cycle".

The rotation and/or displacement of the trajectory should be understood to the effect that at least one point of the trajectory of the first iteration does not correspond to the trajectory of the second iteration. Preferably, at least one measurement point on the trajectory of the first iteration does not correspond to a measurement point on the trajectory of the second iteration. Particularly preferably, the trajectory of the first iteration only intersects the trajectory of the second iteration such that no two adjacent measurement points are captured by the trajectory of the first iteration and the trajectory of the second iteration. The rotation and/or displacement of the trajectory should be understood as a relative movement between the trajectory and the eye.

The rotation and/or displacement of the trajectory should further be interpreted to the effect that one of the following options is present:
  only a rotation of the trajectory; or
  only a displacement of the trajectory; or
  a combination between a rotation and a displacement of the trajectory.

The rotation of the trajectory is understood to mean a rotation of the trajectory about the axis of rotation parallel to the Z-axis, with the axis of rotation preferably extending through a midpoint of the trajectory. Here, the midpoint of the trajectory can be defined in different ways. By way of example, the midpoint may be defined as start or endpoint of the trajectory in relation to an iteration. On the other hand, the midpoint of the trajectory may also be defined as midpoint of a circumference of the trajectory. Particularly preferably, the midpoint lies approximately on the apex, a vector of symmetry or an optical axis of the eye.

The displacement of the trajectory is understood to mean a lateral displacement of the trajectory in the XY-plane.

According to the invention, the trajectory of the first iteration is rotated through an angle and/or displaced by a distance in relation to the trajectory of the second iteration in order to obtain a more homogeneous measurement point distribution. The more homogeneous measurement point distribution is achieved by virtue of at least one measurement point of the second iteration not lying on a measurement point of the first iteration as a result of the rotation or displacement of the trajectory. Particularly preferably, the two trajectories of the first iteration and the second iteration do not have any common adjacent measurement points such that the trajectories only coincide in the form of points of intersection. Hence, a scattering of the measuring points is further increased as a result of the rotation or the displacement.

Since, according to the invention, exactly one trajectory may be used to obtain a more homogeneous measurement point distribution, a particularly simple method for capturing measurement points on an eye is developed, said method moreover also being particularly advantageous in terms of evaluating the measurement data.

Preferably, any straight line extending within the trajectory intersects the trajectory at at least two spaced apart points. Hence, a trajectory which, per se, already has a good measurement point distribution is obtained.

Alternatively, use could also be made of trajectories which are intersected merely at one point by such a straight line.

In the case of a particularly advantageous embodiment of the method, the trajectory is embodied in such a way that:

the measurement point distances have a particularly ideal distribution in the radial direction, in particular in relation to the point of rotation of the trajectory, in the case of a rotation of the trajectory;

the measurement points have a particularly ideal distribution, in particular in a direction crossing the displacement direction, in the case of a displacement of the trajectory.

In the case of a combined movement of the trajectory by way of rotation and displacement, the measurement point distribution of the trajectory may be selected in such a way that the respective contributions of the rotation and of the displacement are taken into account accordingly. By way of example, to the extent that the rotational proportion is large, a homogeneous measurement point distribution may be weighted more in the radial direction, and vice versa.

However, the measurement point distribution on the trajectory may also be largely ignored in variants.

Preferably, an initial point of the second trajectory corresponds to the endpoint of the first trajectory. This allows the measurement method to be carried out continuously, i.e. without jumps. Using this, a continuous measurement, for example with a temporally constant interval, may be carried out with the interferometer. By way of example, this may be achieved by virtue of the same point being selected as initial point and endpoint in each case. By way of example, it may lie at the center of the region.

In variants, it is also possible that the initial point of the second trajectory does not correspond to the endpoint of the first trajectory.

Preferably, the trajectory covers the region. The term "covering" is understood to mean that the region is a portion of the area bounded by the circumference around the trajectory. This already allows substantial measurement of the eye in this region, albeit with a relatively low measurement point density under certain circumstances, during the first iteration of the trajectory. This is advantageous, in particular, if certain conclusions should already be drawn after the first iteration, in particular, for example, if the eye should be localized relative to the measurement appliance.

In variants, the trajectory may also have such a design that it does not cover the region. In this case, the trajectory may e.g. be created in such a way that the region is covered after the second iteration in the case of a suitable rotation and/or displacement. However, the trajectory may also be designed in such a way that coverage is only achieved after more than two iterations, for example after more than 3, 5, 10 iterations.

Preferably, the trajectory is continuously rotated through an angle and/or displaced by a distance. The continuous movement of the trajectory, i.e. the continuous rotation and/or displacement, is advantageous in that the measurement method need not be interrupted during the movement of the trajectory. Hence, the measurement method may be carried out without interruption, facilitating a particularly quick and efficient measurement of an eye. Here, the speed of the measurement is of great interest since this allows movement artifacts of the eye during the measurement to be minimized. Further, it is possible to avoid the case where a discontinuity or a smaller movement radius, which may have a negative influence on the measurement speed, arises in the transition between the iterations. It is thus possible to largely avoid a reduced curve radius with a negative effect on the measurement speed as a result of the continuous or smooth movement of the trajectory during the measurement process.

In variants, the rotation and/or the displacement of the trajectory may also take place between the iterations in each case. In this case, it is particularly advantageous if the initial point of the second iteration and the endpoint of the first iteration correspond and, for example, lie at the center of the trajectory or the region.

In a preferred embodiment, the trajectory of the second iteration is rotated through an angle and/or displaced by a distance in relation to the trajectory of the first iteration only on account of a movement of the eye, as a result of which a more homogeneous measurement point distribution is obtained. A particularly simple measurement method is obtained thus as it is not the trajectory but the eye which is moved. Here, the movement of the eye is preferably the movement of the eye of the subject during the measurement, which typically is not preventable. Minimal movements of the eye are unavoidable, even though the subject e.g. rests his chin during the measurement and presses the forehead against a further support. In these movements, a distinction is made between axial movements (in the Z-axis) and lateral movement (in the XY-plane). The axial movement of the cornea typically lies in a region of 100-200 µm. As a rule, the axial movement tends to be slow and substantially caused by the pulse. The lateral movement of the cornea likewise typically lies in a region of 100-200 µm. The lateral movement consists in approximately equal parts of very small rotations of the eye (slow drift, fast microsaccades, etc.) and lateral head movements. The lateral head movements tend to be slower than the rotations, but have a similar amplitude. These specifications relate to natural movements which cannot be influenced by an ideal subject, i.e. the specifications above tend to lie in the lower range of movements to be expected. In practice, the movements may also be more pronounced. In a particularly preferred method, the trajectory is only rotated and/or displaced on account of the natural eye movement. However, the eye may also be actively moved in a further embodiment, e.g. by virtue of the holder of the head of the subject being moved or by virtue of a fixation light or the like for the eye of the subject being moved. Using this, the movement of the eye may also be influenced actively and a more homogeneous measurement point distribution may possibly be achieved.

In a particularly preferred variant, the movements are actively obtained by the measurement appliance, with the measurement beam being controlled in such a way that the trajectory of the second iteration is rotated through an angle and/or displaced by a distance in relation to the trajectory of the first iteration.

Preferably, the trajectory is rotated through an angle of $m*360°/n$ after each iteration, where m, n≥2 and m≠n. Here, m and n are natural numbers and m is preferably greater than 0. Further, the quotient m/n should trivially be selected between 0 and 1. Preferably, the angle is selected in such a way and the trajectory is fitted in such a way that measurement points which were not captured in the preceding iteration or the preceding iterations are captured in each iteration. This obtains a particularly ideal measurement point density, as a result of which a particularly precise measurement of the eye is obtained in turn. Particularly preferably, the quotient m/n is greater than 0.01, further preferably greater than 0.1, particularly preferably greater than 0.2. As a result of this, the rotated trajectories already obtain a largely regular measurement point distribution after as few iterations as possible. In the case of a quotient of m/n=0.2, the largely regular measurement point distribution would be achieved after e.g. 5 iterations. In the case of a quotient of m/n=0.375, this is already achieved after approximately 3 iterations. In a further advantageous configuration, m/n is selected in such a way that k*m/n is only an integer for large k, where k is a natural number. This further allows a largely regular measurement point distribution to be able to be obtained after a small number of iterations with, however, the identity of the trajectory only being obtained after a large number of iterations. In the example with m/n=0.375, a largely regular measurement point distribution is already achieved after approximately 3 iterations, whereas the identity is only achieved after 8 iterations. Hence, in a preferred method, m and n are co-prime, i.e. GCD(m, n)=1, as a result of which the identity is obtained after n iterations, while a largely regular measurement point distribution is already obtained after $$\left[\frac{n}{m}\right]$$

(n/m rounded up) iterations. By way of example, the value m/n may further be 4/9, 5/9, 7/15, 7/16, 49/128, etc.

In variants, it is also possible to dispense with the rotation of the trajectory. In this case, the trajectory may, for example, only be displaced.

Preferably, the trajectory after the second iteration in relation to the first iteration is rotated through an angle between $$360*0.9*\left(\frac{3-\sqrt{5}}{2}\right)° \text{ and } 360*1.1*\left(\frac{3-\sqrt{5}}{2}\right)°,$$

preferably between $$360*0.95*\left(\frac{3-\sqrt{5}}{2}\right)° \text{ and } 360*1.05*\left(\frac{3-\sqrt{5}}{2}\right)°,$$

particularly preferably between $$360*0.99*\left(\frac{3-\sqrt{5}}{2}\right)° \text{ and } 360*1.01*\left(\frac{3-\sqrt{5}}{2}\right)°,$$

in particular through an angle of approximately $$360*\left(\frac{3-\sqrt{5}}{2}\right)°.$$

Here, the magnitude of $$360*[3-\sqrt{5}]/2$$

corresponds to the golden angle. What is achieved in the ideal case, i.e. if the golden angle is used, is that no iteration is congruent to a preceding iteration. In particular, this causes the measurement point distribution to be increased with each iteration. However, a further advantage of the golden angle is that the increase in the measurement point distribution is substantially uniform. Hence, the measurement method may be interrupted after any number of iterations, without an excessively asymmetric measurement point distribution being risked. As a result, it is also possible to remove sections or entire iterations which were identified as outliers. For the purposes of identifying outliers, the individual iterations are preferably used for modeling the region. In particular, this is possible if the degree of coverage is maintained in the process. By way of example, if a very small angle, such as e.g. 3.6°, were to be selected, an excessively asymmetrical measurement point distribution would be obtained after e.g. 10 iterations in the case of a two-loop trajectory.

However, other angles may also be provided in variants, e.g. 0.375*360° such that, for example, the identity is reached after 8 iterations or 0.4375*360° such that the identity is reached after 16 iterations, etc. (see above).

Preferably, at least a first model of the region is calculated on the basis of the measurement points of the first iteration and a second model of the region is calculated on the basis of the measurement points of the second iteration. Here, these are preferably geometric models. The calculation of the model may comprise the calculation both of the corneal surface and of further planes, such as the corneal rear surface, the lens, etc. The position of the eye may be ascertained particularly easily with the aid of these, preferably geometric models. Then, the position and, optionally, the alignment of the cornea may be determined from the models in each case. Preferably, modeling is carried out by means of Zernike polynomials.

In variants, calculating the model may be dispensed with.

In contrast to traditional photography, by means of which two-dimensional or three-dimensional snapshots may be obtained, the measurement by means of OCT is based on the sequential recording of one-dimensional A-scans. This increases the measurement duration, and so the recordings become susceptible to eye movements, eyelid movements and the like. Hence, there is a risk of the scans being erroneous or incomplete. Hence, the motivation to be able to eliminate movement artifacts is there in the case of OCT measurements.

Therefore, preferably, a spatial curve, which represents the movement of the eye, is calculated on the basis of the at least first model and the second model. The movement trajectory interpolated therefrom may then be applied to the measured points or to the models in order to obtain more accurate modeling. Here, it is particularly advantageous if the individual models, which are typically ascertained in each case on the basis of an iteration or of part of an iteration, have equal status for determining the movement.

In variants, it is also possible to dispense with a calculation of the spatial curve for representing the eye movement.

Preferably, symmetry vectors are determined for the first model and the second model, the spatial curve representing the movement of the eye being calculated on the basis of said symmetry vectors. The symmetry vector is understood to mean a vector, about the axis of which the eye is substantially symmetrical. Typically, this symmetry vector approximately lies in the region of an optical axis of the eye. The symmetry vector may be determined over one or more planes of the eye, such as e.g. corneal front side, corneal rear side, lens surfaces, etc.

In variants, it is possible to dispense with determining symmetry vectors. For the purposes of aligning the eye, it is also possible to identify an asymmetry of the eye which may serve as a reference for the position and alignment of the eye.

Preferably, the movement comprises translational and rotating movement components. Using this, the symmetry vector may capture, firstly, the alignment of the axis of symmetry of the eye and a rotation of the eye. Using this, the symmetry vector may capture, firstly, the alignment of the axis of symmetry of the eye and a rotation of the eye. Overall, this further improves the method for measuring a region of an eye since a movement reconstruction of the eye may be calculated particularly precisely on the basis of these data.

In variants, it is possible to dispense with e.g. the rotating movement portion.

Preferably, a mean model is calculated from the models. Using this method, it is possible to model the region of the eye particularly precisely, in particular since the respective models are based, preferably in a pairwise manner, on at least partly non-common measurement points. A plurality of iterations are measured within the scope of the method. A model, e.g. a model of the cornea, is calculated on the basis of each individual iteration. Further, a position which e.g. may be ascertained by means of a symmetry vector (see above) is determined for each model. A movement trajectory of the eye may be ascertained on the basis of the positions. Subsequently, the positions of the individual models are aligned on the basis of the movement trajectory. Finally, a mean model is calculated on the basis of the aligned models.

In variants, it is also possible to align the individual measurement points of the iterations, which are subsequently combined by calculation to form a model.

In a further preferred method, for the purposes of reducing movement artifacts, measurement points themselves instead of the models are corrected to corrected measurement points on account of the first model and of the second model.

Preferably, for the purposes of correcting the measurement points, the movement trajectory is interpolated on the basis of the positions and orientations of the models in such a way that each measurement point independently results in an interpolated position and alignment of the eye.

In variants, the interpolation may also be dispensed with.

Preferably, the corrected measurement points of the first iteration and of the second iteration are combined to form a cumulative model. The cumulative model thus comprises the measurement points, adjusted by the movement artifacts, of a plurality of iterations, as a result of which a particularly high measurement point density and hence a particularly high precision is obtained when measuring the region of the eye.

In variants, the calculation of the cumulative model on the basis of the individual movement-corrected measurement points may also be dispensed with. In this case, it is possible, for example as explained above, for the individual corrected models to be combined by calculation to form a mean model.

Preferably, the trajectory is passed over in m iterations, where m is selected in such a way that a mean measurement point distance is less than a predetermined expected lateral movement of the eye. In a particularly preferred embodiment, m is selected in such a way that the mean measurement point distance approximately corresponds to the predetermined expected lateral movement of the eye. From this number of iterations, the placement of the new measurement points between the already measured measurement points is random on account of the eye movement, as a result of which it may even be possible, under certain circumstances, to dispense with the displacement and/or rotation of the trajectory.

In variants, m may also be selected to be smaller. In this case, the measurement method could be carried out more quickly but with a lower measurement point density.

When measuring the cornea using OCT, the central region of the cornea is typically scanned at discrete positions. Topography maps of the region may be created on the basis of the measurement points. For the purposes of reconstructing the surface, use is often made of Zernike polynomials. While a $4^{th}$ order Zernike polynomial is sufficient in the case of a normal cornea, the $7^{th}$ or higher order may be required for an abnormal eye. Since the Zernike polynomials moreover lose their orthogonality in the discrete case, the employed scanning pattern has a direct influence on the numerical stability of the reconstruction and limits the order of the Zernike reconstruction.

Preferably, the trajectory has the form of a spiral, in particular a Fermat's spiral; a hypotrochoid; a grid, in particular parallel lines; or of radially arranged loops with a common point of intersection. These forms of the trajectory were found to be particularly advantageous in conjunction with the method according to the invention. The grid-shaped trajectories are particularly simple to scan since only straight lines need to be passed over. However, these are disadvantageous in that relatively small radii must be passed over, as a result of which the speed is typically reduced in these regions. This slows down the scanning process, as a result of which movement artifacts may increasingly occur once again. It was therefore found to be advantageous to use meridional trajectories, which are arranged about a common point, in particular the apex of the eye. Further, an advantage of this method lies in the simplified movement correction since all meridional lines pass through the apex of the eye. On the other hand, disadvantages consist of the fact that, as a rule, no ideal measurement point distribution is achievable, as a result of which the Zernike reconstruction is in turn impaired, and that small radii typically have to be passed over.

Therefore, the form of the trajectory is particularly preferably a Fermat's spiral or a hypotrochoid. These forms have particularly expedient measurement point distributions, wherein the measurement point density may be increased particularly ideally in the case of a suitable rotation of the trajectory and a more stable Zernike reconstruction may be obtained.

Particularly preferably, the trajectory is a Fermat's spiral with the form:

$$r = \pm \theta^{1/2}$$

where r is the radius and θ is the angle of the spiral points in polar coordinates. In a particularly preferred method, the trajectory is fitted in such a way that the radius goes linearly from zero to the radius of the scanning pattern and back again, as a result of which an iteration is defined. This obtains a spiral which goes to the outside, to the inside, etc.

However, other trajectories, in particular other spirals, etc., may be provided in variants.

In a further advantageous embodiment, the trajectory is rotated continuously through an angle in each iteration. If the golden angle is selected to this end, the region is covered by a continuously increased measurement point density, i.e. the mean distance between the measurement points is reduced with each iteration (see above).

However, a person skilled in the art knows of any other desired trajectories which may be used in the present method.

Further, it is also clear to a person skilled in the art that the trajectory is generally not restricted to exactly observing the graphs formed by the formulae. A trajectory or scanning pattern may also deviate from the mathematically correct form. Thus, for example, the family of points ascertained with the measurement beam may only approximately correspond to such a function as an interpolation.

Further advantageous embodiments and feature combinations of the invention emerge from the following detailed description and the totality of the patent claims.

BRIEF DESCRIPTION OF THE DRAWINGS

In the drawings used to explain the exemplary embodiment.

In principle, the same parts are provided with the same reference signs in the figures.

DETAILED DESCRIPTION OF THE INVENTION

Figure 1:
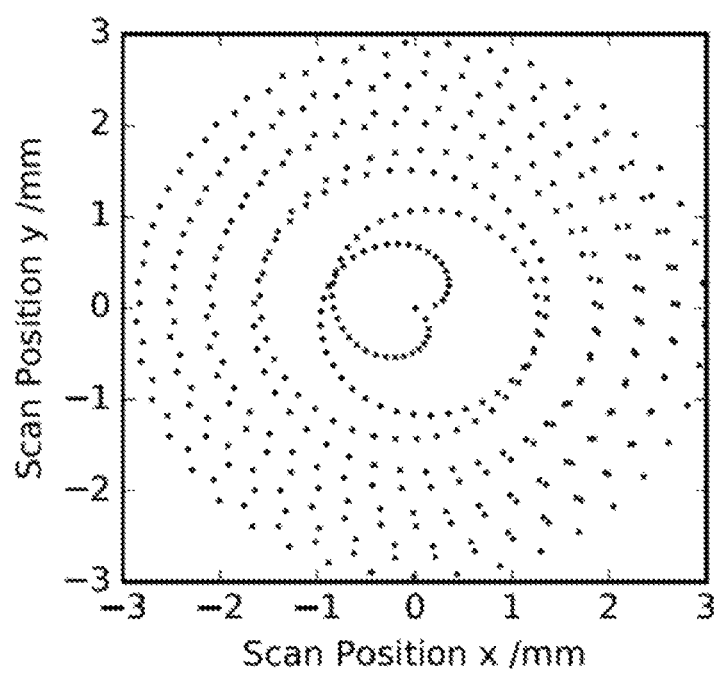
FIG. 1 shows a first cycle of the Fermat's spiral.

In a first preferred embodiment, the trajectory has the form of a Fermat's spiral and it is defined as follows:

$$r = \pm \theta^{1/2}$$

where r is the radius and θ is the angle of the spiral points in polar coordinates. The spiral may be expanded by the following parameters and properties:

R: maximum radius, from which the spiral runs back to the center point.
M: number of rotations for a sweep (denoted by "s" in the index in the following formulae). This number defines how often the spiral runs around the center point before the maximum radius is reached.
$\theta_G$: angle through which the pattern is rotated during an iteration.

Sweep denotes the trajectory from the center point to the reversal point at the edge, and vice versa. Cycle denotes a sweep (respectively abbreviated by s in the index) toward the outside and the subsequent sweep toward the inside. The term "iteration" means the same as the term "cycle".

From this, the following auxiliary parameters emerge for defining the trajectory:

$$\theta_s = M * 2\pi - \frac{\pi}{2} + \frac{\theta_G}{2}$$

$$a = \left(\frac{R^2}{\theta_s}\right)^{1/2}$$

Hence, the following emerges for the Fermat's spiral:

$$r = \begin{cases} a(\theta \bmod \theta_s)^{1/2} & \text{for } \theta \bmod 2\theta_s \leq \theta_s \text{ and } \theta \bmod 4\theta_s \leq 2\theta_s \\ a(\theta_s - (\theta \bmod \theta_s))^{1/2} & \text{for } \theta \bmod 2\theta_s > \theta_s \text{ and } \theta \bmod 4\theta_s \leq 2\theta_s \\ -a(\theta \bmod \theta_s)^{1/2} & \text{for } \theta \bmod 2\theta_s \leq \theta_s \text{ and } \theta \bmod 4\theta_s > 2\theta_s \\ -a(\theta_s - (\theta \bmod \theta_s))^{1/2} & \text{for } \theta \bmod 2\theta_s > \theta_s \text{ and } \theta \bmod 4\theta_s > 2\theta_s \end{cases}$$

The scanning pattern now emerges from the temporal sequence of measurement points or scanning points on the trajectory. A uniform distribution of the points in the area may be achieved by virtue of the scanning points being distributed regularly in θ. If $N_{cycle}$ denotes the number of points per cycle and N denotes the number of measurement points, the following emerges for θ:

$$\theta = \frac{n * 2 * \theta_s}{N_{cycle}} \text{ for } n = 0, 1, 2, \ldots, N.$$

The golden angle is inserted for θ in the ideal case with a theoretically infinite increase in the measurement point density (see above). However, it is usually sufficient in practice for the trajectory to repeat after a finite number of sweeps or cycles or iterations. To this end, e.g. $\theta_G=0.375*2\pi$; M=8; $N_{cycle}$=4096; N=8*4096=32768 could be selected instead of the golden angle. In the case of an A-scan rate of 10 kHz, a measurement would take e.g. 3.28 seconds. The radius of the region of the eye which is measured is typically 3.75 mm, but may also deviate therefrom. As already explained above, it is also possible to select a different number of iterations, measurement points, etc. Likewise, it is possible to use other trajectories than Fermat's trajectory.

FIG. 1 shows, in the XY-plane, a first cycle of the Fermat's spiral in accordance with the example above, with only every tenth measurement point being imaged. The initial point and endpoint of the cycle lie at the apex or in the center. At the center, the end of the cycle coincides with the start of the cycle at an acute angle, which may be traced back to the continuous rotation through the angle of $\theta_G=0.375*2\pi$.

Figure 2:
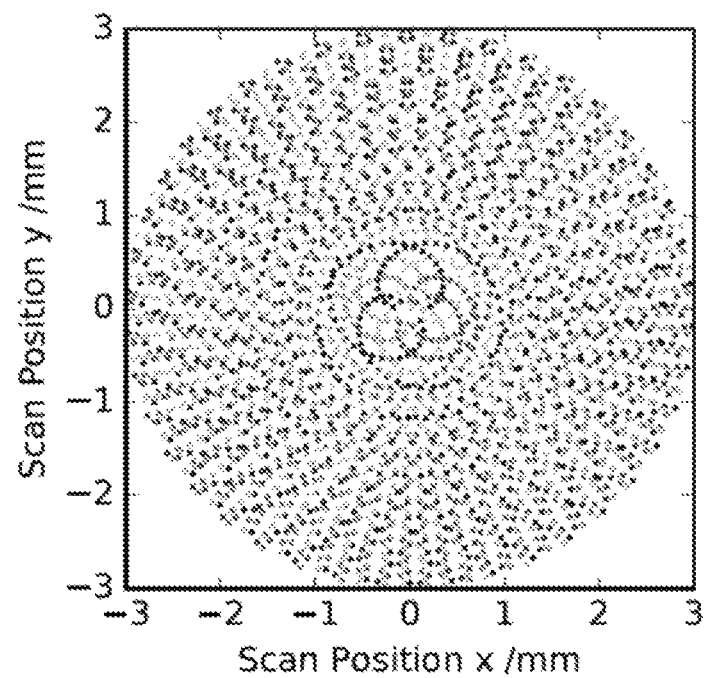
FIG. 2 shows a complete scan with the Fermat's spiral, with eight cycles.

FIG. 2 finally shows the complete scan after eight cycles in the XY-plane. Here, it is possible to see that a very good measurement point distribution has been achieved.

What can be seen particularly well in this exemplary embodiment is that the requirements on the dynamic properties of the OCT scanner are kept relatively low as the radii of curvature of the trajectory are comparatively large over the entire iteration or cycle. In the region of the apex, the trajectory is aligned almost tangentially in relation to the gradient of the cornea. Hence, the ratio between the signal and noise is improved in relation to a conventional grid.

Figure 3:
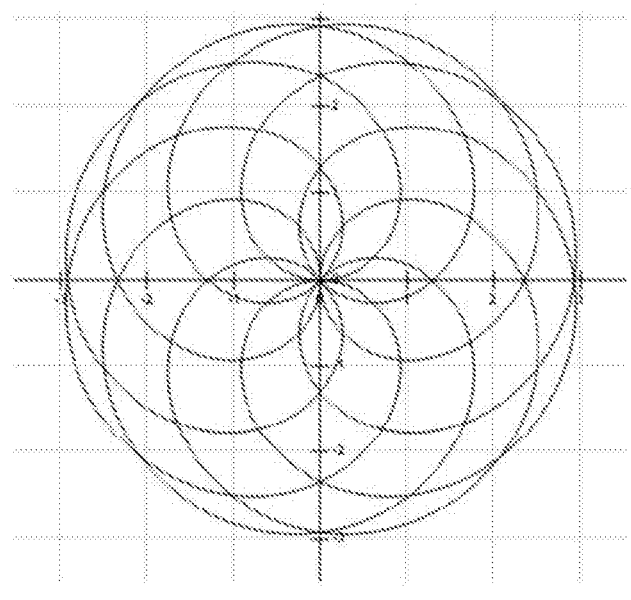
FIG. 3 shows a second embodiment of a possible trajectory.
Figure 4:
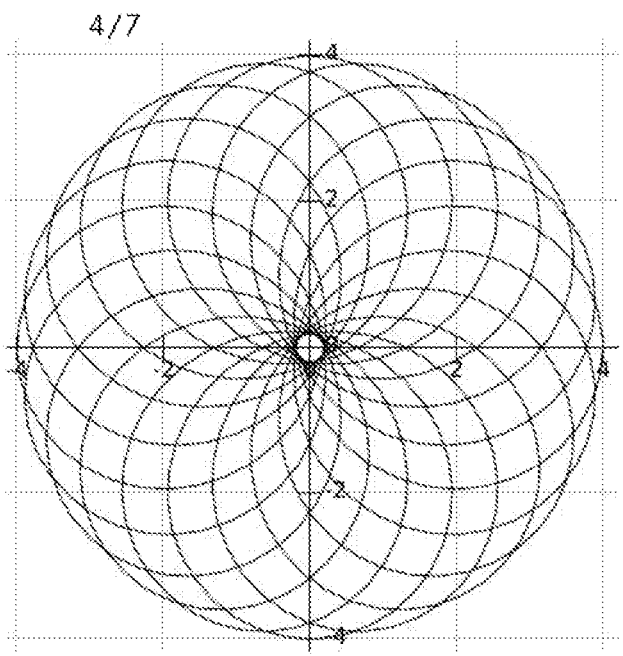
FIG. 4 shows a third embodiment of a possible trajectory.

FIGS. 3 and 4, below, depict further possible trajectories of the general form:

$$x(t)=r_0 \sin(\omega_B t)*\cos(\omega_T t)$$

$$y(t)=r_0 \sin(\omega_B t)*\sin(\omega_T t).$$

Here:
$r_0$: radius of the circumference of the scanning pattern $$\omega_B: \omega_B = 2\pi \frac{B}{2t_{pattern}},$$

$$\omega_T: \omega_T = 2\pi \frac{T}{t_{pattern}}.$$

For the following examples, the measurement duration $t_{pattern}$ is 200 ms (milliseconds). It is clear to a person skilled in the art that, as a matter of principle, a measurement duration which is as short as possible is sought after. However, this depends, firstly, on the employed measurement appliance and, secondly, on the number of measurement points.

In the present case, the number of measurement points equals 3200; the measurement frequency (i.e. the rate at which measurement points are captured) is f=16 kHz. Here, an equilibrium in which the measurement duration is sufficiently small and, at the same time, the number of measurement points and hence, in the case of a constant area to be measured, the resolution are sufficiently high, is sought after.

Furthermore, the measurement frequency is, however, only so large that a sufficient signal strength still emerges for each measurement point as said signal strength decreases with increasing measurement frequency.

FIG. 3 shows an embodiment of a possible trajectory in a particularly preferred form, with B=8 and T=7. From the graph of the function, it can readily be identified that the radius of curvature in each case increases from the edge region toward the center. Moreover, eight points of intersection always lie on a circle concentric with the center of the circumference in each case and the center point is passed through multiple times. Furthermore, it can be seen from the figure that both the edge region and the region near the center may be measured with a high resolution. The scanning pattern has 48 single points of intersection and one eight-fold point of intersection in the center. It is possible to detect and eliminate the eye movement, in particular using the points of intersection away from the center. The high number of points of intersection allows a detection of the eye movement with a correspondingly high frequency (measurement time/number of points of intersection=mean updating time). In the present case, the rotation after each cycle is $\theta_G=0.4375*2\pi$, and so the trajectory is once again present in the original orientation after 16 cycles.

FIG. 4 finally shows, as a further example, a hypotrochoid trajectory as a possible embodiment. The hypotrochoid trajectory has the following general form:

$$x(t) = (a-b)\cos(s) + c*\cos\left(\left(\frac{a-b}{b}\right)*s\right);$$

$$y(t) = (a-b)\sin(s) + c*\sin\left(\left(\frac{a-b}{b}\right)*s\right).$$

For the purposes of ascertaining measurement values in ophthalmology, the values may be selected in such a way that, once again, a radius of approximately 4 mm is achieved. As an example, a=2, b=0.1 and c=2.1 have been selected in FIG. 4. Using this parameterization, a free circle may be identified in the center of the circumference, said free circle having a radius of approximately 0.2 mm. Therefore, this free area satisfies the 0.5 mm criterion specified at the outset.

In the present case, the rotation after each cycle is $\theta_G=0.56*2\pi$, and so the trajectory is once again present in the original orientation after 25 cycles.

In a further exemplary embodiment, use is made of a grid of parallel lines as a trajectory, with the grid being displaced by e.g. 10% of the line spacing in the XY-plane at right angles to a line direction after each iteration. In a further embodiment, there is in each case a displacement by half of the last line spacing, as a result of which it is possible to obtain a continuous refinement of the measurement point distribution. In a further embodiment, the grid is rotated through an angle at each iteration, as explained at the outset. Finally, the grid is both rotated and displaced after each iteration in a further embodiment.

While the trajectory is continuously rotated and/or displaced in each case during the iteration in the exemplary embodiments above, the trajectory may also be rotated and/or displaced between the iterations in each case. However, a consequence of this is that, as a rule, the measurement beam must pass through a relatively large directional change between the iterations, as a result of which, once again, the measurement method is slowed down.

In each of the exemplary embodiments listed above, a model of the region of the eye is advantageously created for the purposes of correcting the movement artifacts after each iteration or after each sweep. A symmetry vector is determined on the basis of the model, by means of which it is also possible to determine the orientation of the eye in respect of a rotation about the symmetry vector and in the XY-plane. A movement trajectory of the eye is preferably obtained subsequently using the plurality of symmetry vectors. Finally, each model of the region of the eye ascertained in advance may be aligned by means of the movement trajectory of the eye. The aligned regions of the eye may once again be combined by calculation in an advantageous manner to form a mean model of the region of the eye. A person skilled in the art knows of any variants for the present correction of the movement artifacts. Thus, the movement trajectory may be used to correct the individual points, etc.

The measurement duration and the number of measurement points may also be smaller or larger, depending on the employed measurement appliance. Depending on the measurement arrangement, it may be advantageous if the measurement duration is shortened, with the smaller resolution being accepted. On the other hand, it is also possible to increase the number of measurement points to the detriment of the measurement duration.

In the present case, the radius of the area to be measured is between 3 and 4 mm. However, this likewise depends on the specific requirements and may, in principle, be selected as required, e.g. 10 mm, 3.5 mm, 1.5 mm and all regions lying therebetween and outside thereof.

In the present case, the axial system resolution of the measurement appliance lies at approximately 4.6 µm, but it may also be higher or lower.

It is clear to a person skilled in the art that the diameter, the number of measurement points and the measurement time may lie in different ranges.

Depending on the measurement system, the measurement frequency may range from a few kHz to several MHz. Measurement frequencies in the range from 10 to 200 kHz were found to be worth pursuing.

Finally, it is also clear to a person skilled in the art that the trajectory is not restricted to exactly observing the graphs formed by the specified mathematical formulae. A trajectory or scanning pattern may also deviate from the mathematically exact form. By way of example, the family of points ascertained with the measurement beam may merely approximately correspond to such a function as an interpolation.

In conclusion, it should be noted that, according to the invention, a method is developed for interferometrically capturing measurement points of a region of an eye, said method permitting a particularly precise capture of the topographies of the region. Further, this achieves a movement correction of the eye in an advantageous manner.

The invention claimed is:

1. A method for interferometrically capturing measurement points of a region of an eye, wherein a plurality of measurement points are captured by a measurement beam along a trajectory, wherein the same trajectory is passed over by the measurement beam in the region during at least a first iteration and a second iteration, wherein the trajectory of the first iteration is rotated through an angle in relation to the trajectory of the second iteration in order to obtain a more homogeneous measurement point distribution, wherein the trajectory after the second iteration in relation to the first iteration is rotated through an angle between $$360*0.9*\left(\frac{3-\sqrt{5}}{2}\right)° \text{ and } 360*1.1*\left(\frac{3\sqrt{5}}{2}\right)°,$$

preferably between $$360*0.95*\left(\frac{3-\sqrt{5}}{2}\right)° \text{ and } 360*1.05*\left(\frac{3-\sqrt{5}}{2}\right)°,$$

particularly preferably between $$360*0.99*\left(\frac{3-\sqrt{5}}{2}\right)° \text{ and } 360*1.01*\left(\frac{3-\sqrt{5}}{2}\right)°,$$

in particular through an angle of approximately $$360*\left(\frac{3-\sqrt{5}}{2}\right)°.$$

2. Method according to claim 1, wherein any straight line extending within the trajectory intersects the trajectory at at least two spaced apart points.

3. Method according to claim 1, wherein an initial point of the second trajectory corresponds to the endpoint of the first trajectory.

4. Method according to claim 1, wherein the trajectory covers the region.

5. Method according to claim 1, wherein the trajectory is continuously rotated through an angle and/or displaced by a distance.

6. Method according to claim 1, wherein the trajectory of the second iteration is rotated through an angle and/or displaced by a distance in relation to the trajectory of the first iteration only on account of a movement of the eye, as a result of which a more homogeneous measurement point distribution is obtained.

7. Method according to claim 1, wherein at least a first model of the region is calculated on the basis of the measurement points of the first iteration and a second model of the region is calculated on the basis of the measurement points of the second iteration.

8. Method according to claim 7, wherein a spatial curve, which represents the movement of the eye, is calculated on the basis of the at least first model and the second model.

9. Method according to claim 8, wherein symmetry vectors are determined for the first model and the second model, the spatial curve representing the movement of the eye being calculated on the basis of said symmetry vectors.

10. Method according to claim 9, wherein the movement comprises translational and rotating movement components.

11. Method according to claim 7, wherein a mean model is calculated from the models.

12. Method according to claim 7, wherein, for the purposes of reducing movement artifacts, measurement points are corrected to corrected measurement points on account of the first model and of the second model.

13. Method according to claim 7, wherein the at least first model and the second model are interpolated for the purposes of correcting the measurement points.

14. Method according to claim 13, wherein the corrected measurement points of the first iteration and of the second iteration are combined to form a cumulative model.

15. Method according to claim 1, wherein the trajectory is passed over in m iterations, where m is selected in such a way that a mean measurement point distance is less than a predetermined expected lateral movement of the eye.

16. Method according to claim 1, wherein the trajectory has the form of
 a. a spiral, in particular a Fermat's spiral;
 b. a hypotrochoid;
 c. a grid, in particular parallel lines; or of
 d. radially arranged loops with a common point of intersection.

17. Apparatus for carrying out a method according to claim 1.

18. Method for interferometrically capturing measurement points of a region of an eye, wherein a plurality of measurement points are captured by a measurement beam along a trajectory, wherein the same trajectory is passed over by the measurement beam in the region during at least a first iteration and a second iteration, wherein the trajectory of the first iteration is rotated through an angle in relation to the trajectory of the second iteration in order to obtain a more homogeneous measurement point distribution, wherein the trajectory after the second iteration in relation to the first iteration is rotated through an angle between $$360*0.9*\left(\frac{3-\sqrt{5}}{2}\right)° \text{ and } 360*1.1*\left(\frac{3-\sqrt{5}}{2}\right)°.$$

19. The method according to claim 18, wherein the trajectory after the second iteration in relation to the first iteration is rotated through an angle between $$360*0.95*\left(\frac{3-\sqrt{5}}{2}\right)° \text{ and } 360*1.05*\left(\frac{3-\sqrt{5}}{2}\right)°.$$

20. The method according to claim 19, wherein the trajectory after the second iteration in relation to the first iteration is rotated through an angle between $$360*0.99*\left(\frac{3-\sqrt{5}}{2}\right)° \text{ and } 360*1.01*\left(\frac{3-\sqrt{5}}{2}\right)°.$$

21. The method according to claim 20, wherein the trajectory after the second iteration in relation to the first iteration is rotated through an angle of approximately $$360*\left(\frac{3-\sqrt{5}}{2}\right)°.$$

* * * * *